US00PP37452P2

(12) United States Plant Patent
Lee

(10) Patent No.: US PP37,452 P2
(45) Date of Patent: Jun. 2, 2026

(54) ***GARDENIA* PLANT NAMED 'LEEIGHT'**

(50) Latin Name: *Gardenia hybrida*
Varietal Denomination: LEEIGHT

(71) Applicant: Robert Edward Lee, Independence, LA (US)

(72) Inventor: Robert Edward Lee, Independence, LA (US)

(73) Assignee: PDSI, Loxley, AL (US)

( * ) Notice: Subject to any disclaimer, the term of this patent is extended or adjusted under 35 U.S.C. 154(b) by 0 days.

(21) Appl. No.: 18/978,584

(22) Filed: Dec. 12, 2024

(51) Int. Cl.
*A01H 5/02* (2018.01)
*A01H 5/12* (2018.01)
*A01H 6/76* (2018.01)

(52) U.S. Cl.
USPC ..... Plt./255
CPC ..... *A01H 6/76* (2018.05); *A01H 5/02* (2013.01); *A01H 5/12* (2013.01)

(58) Field of Classification Search
USPC ..... Plt./226, 255
See application file for complete search history.

(56) References Cited

U.S. PATENT DOCUMENTS

PP31,017 P2 * 11/2019 Head ..... A01H 6/76
Plt./206

* cited by examiner

*Primary Examiner* — Karen M Redden

(57) ABSTRACT

A new and distinct cultivar of *Gardenia* plant named 'LEEIGHT' is disclosed, characterized by dark green, glossy foliage with irregular pale yellow variegation. Flowers are fragrant, profuse single blooms, occurring in the Spring and again in the Fall. Plants have a low, mounding growth habit, growing to 2.5 to 3.5 feet in diameter. This growth habit is easy to maintain with occasional pruning, making the new cultivar well suited for container use, or as a specimen in the garden. The new cultivar is a *Gardenia*, suitable for ornamental purposes.

2 Drawing Sheets

Figure 1:
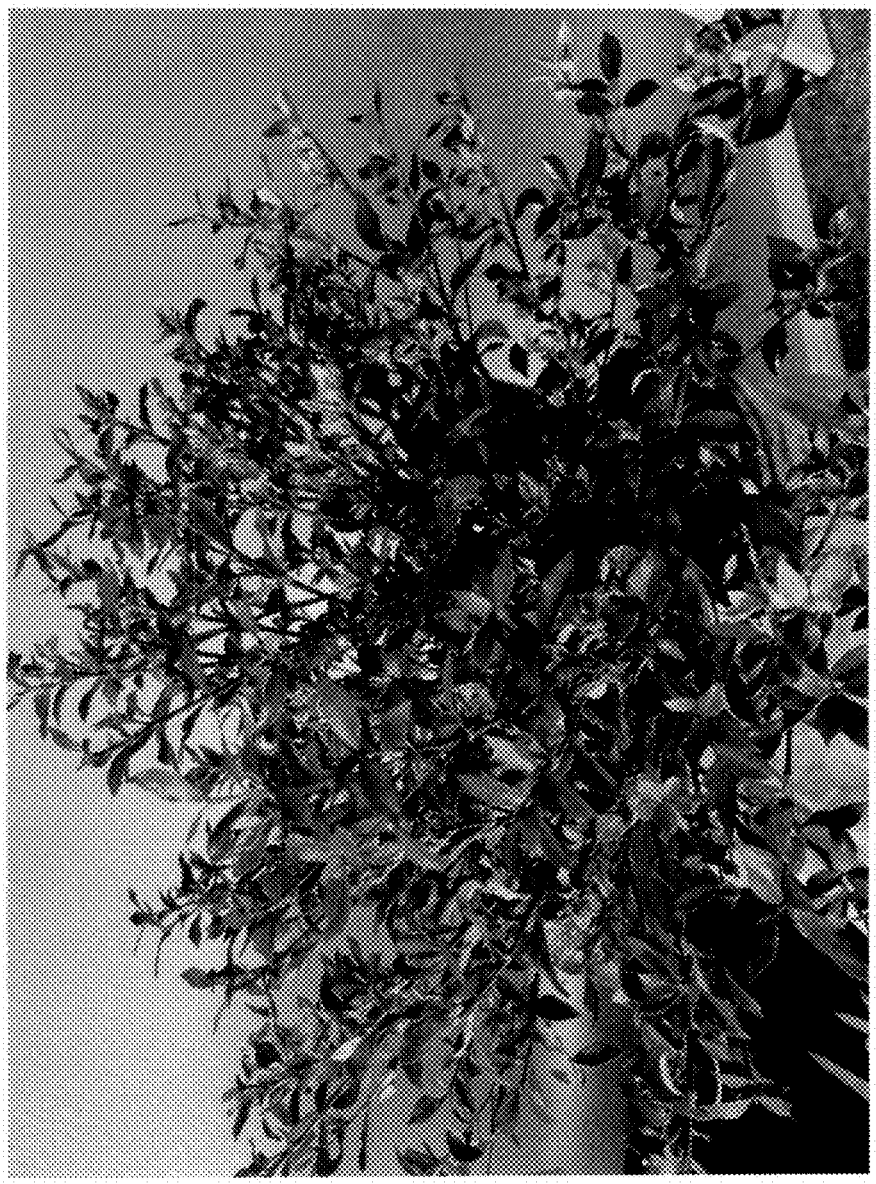

Latin name of the genus and species: *Gardenia hybrida*. Variety denomination: 'LEEIGHT'.

BACKGROUND OF THE INVENTION

The new cultivar is a product of a planned breeding program by the inventor with the intention to develop *Gardenia* cultivars with superior stable leaf variegation. This new variety, hereinafter referred to as 'LEEIGHT', was found as the result of an open-pollination conducted between approximately 2014 and 2018. The inventor established crossing blocks of proprietary, unpatented seedlings of *Gardenia radicans* x *jasminoides* which he had selected from a 2012 crossing. The inventor discovered the unique seedling in Independence, Louisiana, at a research nursery during 2018.

After identifying the new variety as a potentially interesting selection, the inventor first propagated 'LEEIGHT' by semi-hardwood cuttings during Fall of 2018 at the same nursery in Independence, Louisiana. The inventor continued confidential, controlled testing and propagation, assessing stability of the unique characteristics of this variety. Multiple generations have been reproduced and have shown that the unique features of this cultivar are stable and reproduced true to type.

SUMMARY OF THE INVENTION

The cultivar 'LEEIGHT' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'LEEIGHT' These characteristics in combination distinguish 'LEEIGHT' as a new and distinct *Gardenia* cultivar:

1. Fragrant, profuse single blooms, occurring in the Spring and again in the Fall.
2. Low, mounding growth habit.
3. 2.5 to 3.5 feet in width, easy to maintain with occasional pruning.
4. Dark green, glossy foliage with irregular pale yellow variegation.
5. Good specimen plant.
6. Good container plant.

COMPARISON TO PARENT VARIETY

The parent varieties are unidentified.

COMMERCIAL COMPARISON

'LEEIGHT' can be compared to the commercial variety *Gardenia radicans* 'Variegata', unpatented. Plants of the new cultivar 'LEEIGHT' are similar to plants of 'Variegata' in most horticultural characteristics, however, plants of the new cultivar 'LEEIGHT' differ in the following:

1. While both plants have compact growth, the new variety grows more vigorously and becomes about 30% taller and wider than this comparator.

2. 'LEEIGHT' reblooms in the Fall; 'Variegata' does not rebloom.
3. Foliage of the new cultivar is larger than foliage of this comparator.

'LEEIGHT' can be compared to the commercial variety *Gardenia hybrida* 'Mystery Variegated', unpatented. Plants of the new cultivar 'LEEIGHT' are similar to plants of 'Mystery Variegated' in most horticultural characteristics, however, plants of the new cultivar 'LEEIGHT' differ in the following:

1. 'Leeight' has a low, mounding habit; plants of 'Mystery Variegated' grow to 5 feet tall.
2. 'LEEIGHT' reblooms in the Fall; 'Mystery Variegated' blooms only in the Summer.

BRIEF DESCRIPTION OF THE PHOTOGRAPHS

The accompanying photograph in FIG. 1 illustrates in full color a plant of 'LEEIGHT' grown outdoors in Loxley, Alabama.

Figure 2:
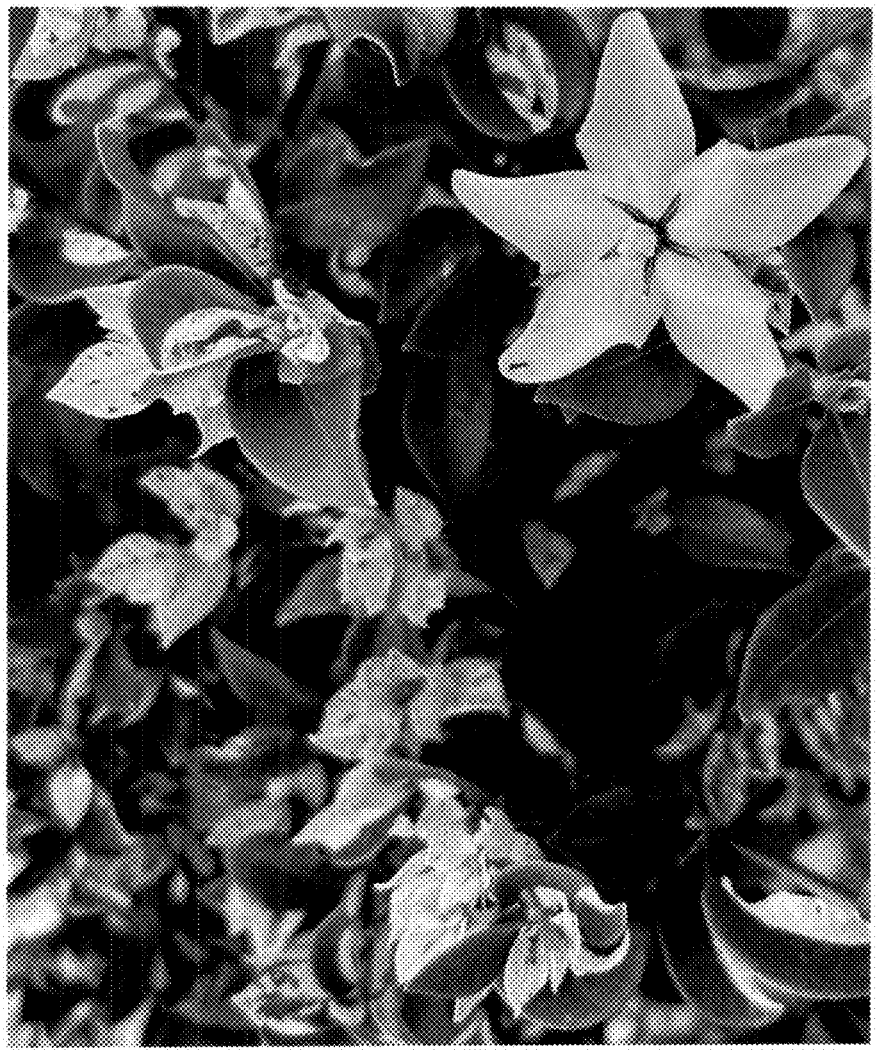

FIG. 2 shows a close up of a typical flower of the new variety.

The plant is approximately 2 years old, and is shown in a three-gallon container. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'LEEIGHT' plants grown outdoors in Loxley, Alabama. Plants are approximately 2 years old, in a 5-gallon nursery container. Measurements and numerical values represent averages of typical plant types.

Botanical classification: *Gardenia radicans* x *jasminoides* 'LEEIGHT'.

PROPAGATION

Typically by semi-hardwood cuttings in Spring and Summer.

Root description: Woody to semi-wood. Colored near RHS Brown 200D.

Time to initiate roots: About 4 to 6 weeks in the Summer.

Time to produce a rooted young plant: Approximately 12 weeks in the Summer.

PLANT

Growth habit: Low, mounding, evergreen flowering shrub.

Height: Approximately 40 cm.

Plant spread: Approximately 65 cm.

Branching characteristics: Well branched, approximately 4 to 7 lateral branches emerge from a pinch. Smaller lateral branches occurring along main stems. Branches occur at approximately 35° to 75° angles.

Primary branches:

Length of primary branches: Average range 8 to 12 cm then splitting into smaller laterals.

Diameter of primary branches: Average range 11 to 16 mm.

Primary branch strength: Very strong.

Primary branch color: Near RHS Grey-Brown N199B striated Brown N200A. Lowest section most heavily striated.

Primary branch texture: Striated to very slightly scaly.

Lateral branches:

*Color*.—New growth near RHS Green 143C. Mature growth Greyed-Purple N186C with overlayer N187C.

*Length*.—Average range 15 to 35 cm.

*Diameter*.—Approximately 3 to 5 mm.

*Aspect*.—Straight.

*Texture*.—Very slightly rough.

*Strength*.—Strong, flexible.

*Internode*.—Average range 2.5 to 3.5 cm

Age of plant described: Approximately 2 years.

FOLIAGE

Leaf:

*Type*.—Simple.

*Arrangement*.—Opposite.

*Average length*.—Average range 4.0 cm to 6.5 cm.

*Average width*.—Approximately 2.5 cm.

*Shape of blade*.—Broad elliptic.

*Apex*.—Acute.

*Base*.—Attenuate.

*Attachment*.—Sessile.

*Margin*.—Entire.

*Internode*.—Average 2.5 cm.

*Texture of top surface*.—Glabrous.

*Texture of bottom surface*.—Glabrous.

*Appearance of top surface*.—Glossy.

*Appearance of bottom surface*.—Matte.

*Color*.—Young foliage upper side: Variable. About 70% of new foliage Yellow 4D with about 20%-30% coverage in Green 137A flecks. About 20% of new foliage Green 137A with central flecks yellow 4D, near central vein. About 10% of new foliage Yellow 2D, with about 10 small marginal flecks near Green 137A. Young foliage under side: Variable. About 70% of new foliage Yellow 4D with about 20%-30% coverage in Green 137C flecks. About 20% of new foliage Green 137C with central flecks yellow 4D, near central vein. About 10% of new foliage Yellow 2D, with about 10 small marginal flecks near Green 137C. Mature foliage upper side: About 70% of foliage Green 137C with Yellow 4D variegation. Mature foliage under side: Mature foliage upper side: About 70% of foliage Green 137C with Yellow 2D variegation.

*Venation*.—Type: Pinnate. Venation color upper side: Near RHS Yellow-Green 145D. Venation color under side: Near RHS Yellow-Green 145D.

FLOWER

Bloom period: Plants flower in the Spring and rebloom in the Fall.

Inflorescence:

*Arrangement*.—Single rotate flowers arise from upper leaf axils.

Peduncle:

*Length*.—Average range 1 to 2 cm.

*Diameter*.—5 mm.

*Color*.—Near RHS Green 143C.

*Texture*.—Glabrous.

*Aspect*.—Straight. Angle of attachment, approximately 0 to 15° angle from stem.
*Strength*.—Strong and flexible.

Flowers:
*Arrangement*.—Single rotate flowers arise from upper leaf axils.
*Length*.—Average 3 cm.
*Diameter*.—Average 5 to 6 cm.
*Facing direction*.—Outwardly and upwardly facing.
*Persistent or self-cleaning*.—Flowers persist until completely dried up, then fall off.
*Fragrance*.—Strong, sweet fragrance.

Tube:
*Tube length*.—Approximately 2.5 cm.
*Tube width a widest point*.—Approximately 4 mm.
*Tube width and narrowest point*.—Approximately 3 mm.

Petals:
*Unfused petal segments*.—
*Length*.—Approximately 2.5 cm.
*Width*.—Approximately 1.5 cm.
*Apex*.—Tapered, then founded.
*Base*.—Fused at base into tube.
*Shape of petal*.—Unfused portion, deltate.
*Petal margin*.—Entire.
*Petal arrangement*.—Rotate, very slightly overlapping, or not overlapping fused approximately ¼ from base.
*Petal number*.—5.
*Petal texture*.—Smooth, upper and lower surfaces.
*Color*.—Upper surface at first opening: Near RHS White 155C. Under surface at first opening: Near RHS White 155C. Inner surface at maturity: Near RHS White 155C. Outer surface at maturity: Near RHS White 155C. Upper surface at fading: Near RHS White 155C. Under surface at fading: Near RHS White 155C.

Bud:
*Shape*.—Elliptic.
*Length*.—2.5 cm.
*Diameter*.—1.5 cm.
*Color*.—Near RHS White 155C and Yellow-Green 145D.

Calyx/sepals:
*Quantity per flower*.—5 sepals.
*Arrangement*.—Rotate.
*Shape*.—Narrow deltate, base fused.
*Length*.—Average 9 mm.
*Width*.—3 mm.
*Apex*.—Acute.
*Base*.—Fused.
*Margin*.—Entire.
*Texture*.—Very slightly pubescent all surfaces.
*Color*.—Inner Surface: Near RHS Green 143C. Outer Surface: Near RHS Green 143B.

REPRODUCTIVE ORGANS

Stamens:
*Number*.—5, except anthers, androecium fused to floral tube.
*Length*.—7 mm, anthers only.
*Width*.—1 mm.
*Anthers*.—Anthers reflexed back, and attached to petals. Length: Approximately 7 mm. Width: Approximately 2 mm.
*Color*.—Near RHS Greyed-Orange 166A, center streak Yellow-White 158D. Pollen: Scant, colored near RHS Greyed-Orange 165D. Shape: Linear.

Pistil:
*Number*.—1.
*Length*.—3.5 cm.
*Style*.—Length: 3. cm. Color: Near RHS Yellow-Green 150D.
*Stigma*.—4 lobed globular, colored near RHS Yellow-White 158A.
*Ovary*.—Approximately 3 mm in diameter, 3 mm long. Colored near RHS Green 143C.

OTHER CHARACTERISTICS

Disease and pest resistance: Neither resistance nor susceptibility observed to normal diseases and pests of *Gardenia hybrida*. Typical diseases of *Gardenia* include *Erysiphe polygoni*, and *Phomopsis gardenia*. Pests include the nematode *Meloidogyne* spp., white fly *Dialeurodes citri* and various scales, including *Ceroplastes japonicas, Icerya purchase, Fiorinia theae, Hemiberlesia rapax* and *Aspidiotus nerii*.

Temperature tolerance: USDA Zone 7 to 10.

Fruit/seed production: Not observed to date.

What is claimed is:

1. A new and distinct cultivar of *Gardenia* plant named 'LEEIGHT' as herein illustrated and described.

* * * * *